United States Patent
Ooishi et al.

(10) Patent No.: US 10,889,541 B2
(45) Date of Patent: Jan. 12, 2021

(54) METHOD FOR PRODUCING N-VINYLFORMAMIDE

(71) Applicant: Mitsubishi Chemical Corporation, Chiyoda-ku (JP)

(72) Inventors: Noritsugu Ooishi, Tokyo (JP); Kouji Teramoto, Tokyo (JP); Yasuharu Mori, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/360,907

(22) Filed: Mar. 21, 2019

(65) Prior Publication Data

US 2019/0218173 A1    Jul. 18, 2019

Related U.S. Application Data

(63) Continuation of application No. PCT/JP2017/039532, filed on Nov. 1, 2017.

(30) Foreign Application Priority Data

Nov. 1, 2016 (JP) ................................. 2016-214182

(51) Int. Cl.
  *C07C 231/12* (2006.01)
  *C07C 233/03* (2006.01)
(52) U.S. Cl.
  CPC .......... *C07C 231/12* (2013.01); *C07C 233/03* (2013.01)
(58) Field of Classification Search
  None
  See application file for complete search history.

(56) References Cited

U.S. PATENT DOCUMENTS 5,527,963 A * 6/1996 Sato ...................... C07C 231/12
                                            564/187

FOREIGN PATENT DOCUMENTS

JP    3-181451    8/1991
JP    3-181452    8/1991
(Continued)

OTHER PUBLICATIONS

International Search Report dated Jan. 16, 2018 in PCT/JP2017/039532, filed on Nov. 1, 2017 (with English Translation).
(Continued)

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A method for producing N-vinylformamide through a vapor-phase thermal decomposition reaction using an evaporator (10) for evaporating a raw material, a thermal decomposition reactor (20) for thermally decomposing a raw material gas generated by the evaporator (10) and a condenser (30) for condensing a thermally decomposed gas generated by the thermal decomposition reactor (20), wherein the evaporation of the raw material is started in the evaporator (10) while the temperature of a tube wall of a first connection tube (40) that connects the evaporator (10) to the thermal decomposition reactor (20) satisfies a requirement represented by formula (1): (temperature of tube wall (° C.))≥0.37×(pressure of evaporator (mmHg))+205.

10 Claims, 1 Drawing Sheet

(56) References Cited

FOREIGN PATENT DOCUMENTS

| JP | 5-301851 | 11/1993 |
|----|----------|---------|
| JP | 2012-140392 | 7/2012 |

OTHER PUBLICATIONS

Extended European Search Report dated Sep. 27, 2019 in European Patent Application No. 17867166.5, 5 pages.
European Office Action dated Aug. 17, 2020, in European Patent Application No. 17867166.5.

* cited by examiner

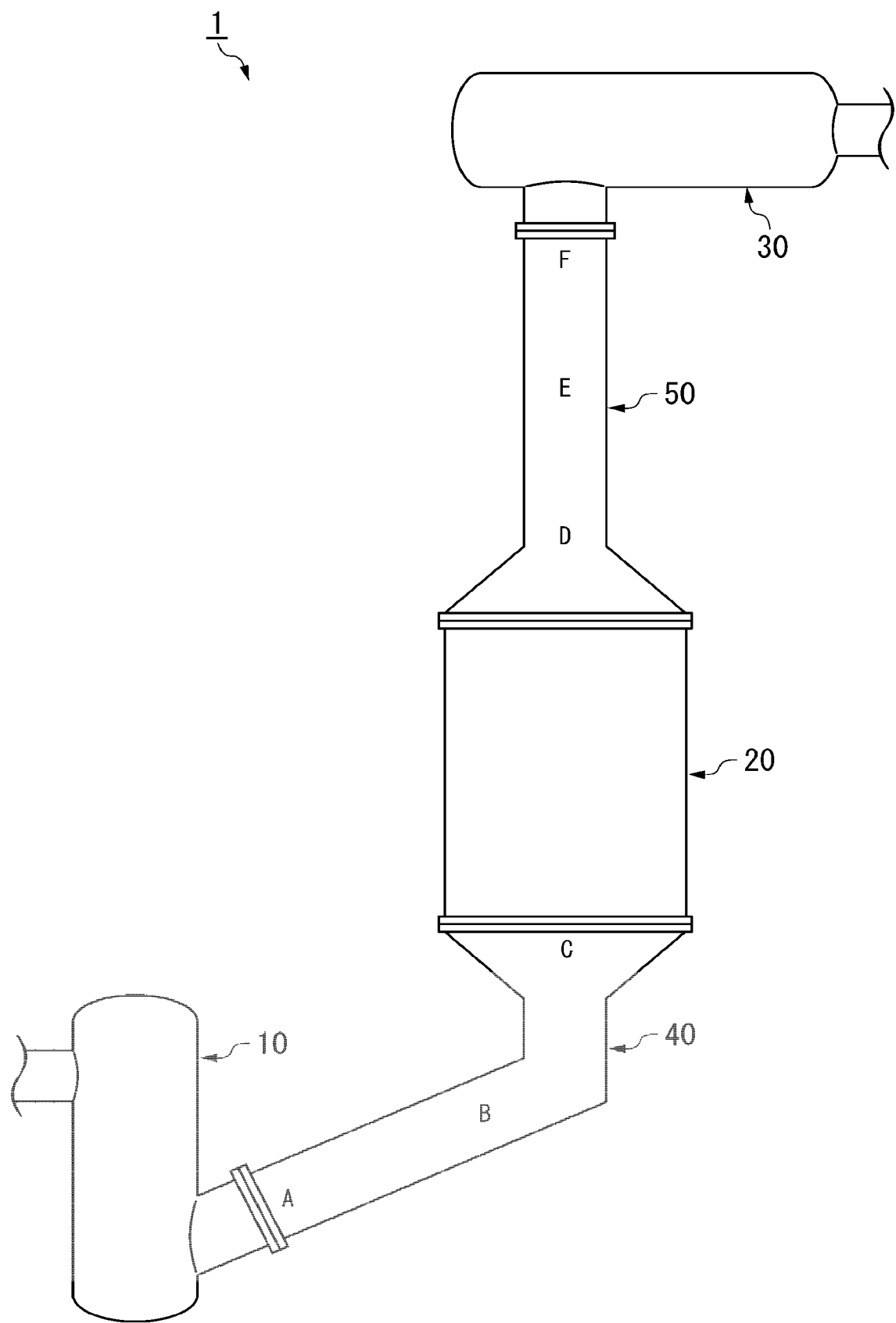

METHOD FOR PRODUCING N-VINYLFORMAMIDE

The present invention relates to a method for producing N-vinylformamide.

TECHNICAL FIELD

This application is a continuation application of International Application No. PCT/JP2017/039532, filed on Nov. 1, 2017, which claims the benefit of priority of the prior Japanese Patent Application No. 2016-214182 filed in Japan on Nov. 1, 2016, the entire contents of which are incorporated herein by reference.

BACKGROUND ART

N-vinylformamide is an important substance as a raw material monomer of a polymer to be used in applications such as aggregating agents, papermaking chemicals, fiber treatment agents, and paint additives.

As a method for producing N-vinylformamide, for example, a method is known in which a raw material such as a N-(α-substituted-ethyl)formamide is evaporated in an evaporator to obtain a raw material gas, this raw material gas is subjected to vapor phase thermal decomposition in a thermal decomposition reactor, and the thermally decomposed gas obtained is condensed in a condenser.

However, in the case of the method described above, a condensation product of N-vinylformamide (tar-like or solid-state resin) has been formed by a side reaction in some cases. Moreover, the condensation product adheres to the inner wall of the connecting pipe which connects the evaporator with the thermal decomposition reactor, thus the connecting pipe is clogged, and it is difficult to conduct stable working in some cases. It is also known that the quality of N-vinylformamide gradually deteriorates when the condensation product gradually accumulates in the connecting pipe. Here, deterioration in quality refers to the deterioration in storage stability of a monomer, a decrease in the polymerization activity, that is, delay of initiation of polymerization, a decrease in the molecular weight of polymer to be obtained by polymerization, an increase of residual monomers, an increase of insoluble components, and the like.

Accordingly, a method for preventing adhesion of a condensation product of N-vinylformamide to, for example, the inner wall of the connecting pipe which connects the evaporator with the thermal decomposition reactor is known. For example, a method using a production apparatus in which an evaporator is connected with a thermal decomposition reactor via a connecting pipe having an upward inclined portion at least at a part and a resin-storing container opened to the connecting pipe is connected to the inclined portion of the connecting pipe has been proposed (Patent Document 1 and the like).

CITATION LIST

Patent Document

Patent Document 1: JP 2012-140392 A

SUMMARY OF THE INVENTION

Problem to be Solved by the Invention

According to the method described in Patent Document 1, a condensation product of N-vinylformamide is allowed to flow down in the upward inclined portion of the connecting pipe and collected in the resin-storing container to prevent the condensation product from adhering to the connecting pipe.

However, there is a limit in the prevention of adhesion of condensation product by the method described in Patent Document 1 as a measure, and thus the condensation product adheres to the connecting pipe to some extent since the formation of the condensation product itself is not suppressed, it is difficult to allow the condensation product to flow down when the condensation product is in the state of adhering to the connecting pipe for a long period of time, the storage stability and polymerization quality of N-vinylformamide gradually deteriorate when the working is conducted for a long period of time in the presence of adhered substances, and the resin-storing container is required to be periodically cleaned.

Means for Solving Problem

Accordingly, the inventors of the invention have attempted to prevent clogging of the connecting pipe by suppressing the formation of condensation products rather than suppressing the adhesion of condensation products formed to the connecting pipe.

The invention has been made in view of the above circumstances, and an object thereof is to provide a method for producing N-vinylformamide by which it is possible to suppress the formation of a condensation product and to stably produce N-vinylformamide.

The invention has the following aspects.

[1] A method for producing N-vinylformamide by a vapor phase thermal decomposition reaction using an evaporator for evaporating a raw material, a thermal decomposition reactor for thermally decomposing a raw material gas generated by the evaporator, and a condenser for condensing a thermally decomposed gas obtained by the thermal decomposition reactor, in which evaporation of the raw material in the evaporator is started in a state in which a temperature of a pipe wall of a first connecting pipe for connecting the evaporator with the thermal decomposition reactor satisfies the following Equation (1).

$$\text{temperature of pipe wall (° C.)} \geq 0.37 \times \text{pressure of evaporator (mmHg)} + 205 \quad \text{Equation (1):}$$

[2] The method for producing N-vinylformamide according to [1], in which evaporation of the raw material in the evaporator is started in a state in which a temperature of a pipe wall of a second connecting pipe for connecting the thermal decomposition reactor with the condenser satisfies Equation (1) above.

[3] The method for producing N-vinylformamide according to [1] or [2], in which the raw material is a N-(α-substituted-ethyl)formamide.

[4] The method for producing N-vinylformamide according to [3], in which the N-(α-substituted-ethyl)formamide is a N-(α-alkoxyethyl)formamide.

[5] The method for producing N-vinylformamide according to [2], in which evaporation of the raw material in the evaporator is started in a state in which temperatures of pipe walls of the first connecting pipe and the second connecting pipe satisfy the following Equation (2).

$$\text{temperature of pipe wall (° C.)} \geq 0.37 \times \text{pressure of evaporator (mmHg)} + 210 \quad \text{Equation (2):}$$

[6] The method for producing N-vinylformamide according to any one of [1] to [5], in which a temperature of a pipe wall of the thermal decomposition reactor is higher than a temperature of a reaction gas passing through the thermal decomposition reactor.

[7] The method for producing N-vinylformamide according to any one of [1] to [5], in which a temperature of a heating medium of the thermal decomposition reactor is higher than the temperature of the pipe wall of the first connecting pipe by 10° C. or more.

[8] The method for producing N-vinylformamide according to [2], in which temperatures of pipe walls of the first connecting pipe and the second connecting pipe are less than 600° C.

Effect of the Invention

According to the method for producing N-vinylformamide of the invention, it is possible to suppress the formation of a condensation product and to stably produce N-vinylformamide. Stopping for cleaning the resin-storing container and the first connecting pipe and restarting operation are unnecessary, thus there is no possibility of a decrease in the production amount and a fluctuation in the quality which result from the stopping and restarting operation and the cost of plant repair such as cleaning can also be cut down. In addition, it is also possible to suppress a decrease in the quality and a fluctuation in the stability of N-vinylformamide which result from the decomposition products to be volatilized from the condensation product adhered and the condensation product flowed down in the container. Furthermore, it is possible to prevent loss of raw material due to the formation of a condensation product, and the yield of N-vinylformamide is thus improved.

BRIEF DESCRIPTION OF DRAWINGS

FIG. 1 is a schematic configuration diagram illustrating an example of an apparatus for producing N-vinylformamide which is used in the method for producing N-vinylformamide of the invention.

MODE(S) FOR CARRYING OUT THE INVENTION

Hereinafter, the invention will be described in detail with reference to FIG. 1.

FIG. 1 is a schematic configuration diagram illustrating an example of an apparatus for producing N-vinylformamide (hereinafter also simply referred to as the "production apparatus") which is used in the method for producing N-vinylformamide of the invention.

In FIG. 1, a production apparatus 1 is equipped with an evaporator 10 for evaporating a raw material of N-vinylformamide, a thermal decomposition reactor 20 for thermally decomposing a raw material gas (vaporized raw material) generated by the evaporator 10, a condenser 30 for condensing a thermally decomposed gas (reaction gas) to be obtained by the thermal decomposition reactor 20, a first connecting pipe 40 for connecting the evaporator 10 with the thermal decomposition reactor 20, and a second connecting pipe 50 for connecting the thermal decomposition reactor 20 with the condenser 30.

Incidentally, in the following description, the raw material gas and the thermally decomposed gas are collectively referred to as the "process gas".

1. Raw Material

Examples of the raw material may include a N-(α-substituted-ethyl)formamide and ethylidene bis(formamide). Among these, a N-(α-substituted-ethyl)formamide is preferable from the viewpoint of being easy to separate N-vinylformamide from by-products and from the viewpoint that the boiling point thereof is not too high and it is easily gasified and introduced into the thermal decomposition reactor.

Here, the term "α-substituted-ethyl" means that the carbon at the first position in the ethyl group has a substituent.

Examples of the α-substituent may include lower alkoxy groups such as a methoxy group, an ethoxy group, a propoxy group, an isopropoxy group, a butoxy group, a s-butoxy group, and a t-butoxy group; higher alkoxy groups such as (poly)ethylene glycol and (poly)propylene glycol; and a cyano group.

Among these, a N-(α-alkoxyethyl)formamide is preferable from the viewpoint that hydrogen cyanide is not generated and a N-(α-alkoxyethyl)formamide having a lower alkoxy group is particularly preferable from the viewpoint of being easily evaporated.

As the raw material gas, the N-(α-alkoxyethyl)formamide may be evaporated as it is and introduced into the thermal decomposition reactor or it may be diluted with an inert gas and introduced. Furthermore, the raw material gas may contain a third component which does not inhibit the reaction of an alcohol, formamide, and the like. The proportion of the N-(α-alkoxyethyl)formamide in the raw material gas is 10% by mass or more, preferably 50% by mass or more, and still more preferably 80% by mass or more.

The raw material gas may be diluted with an inert gas and the partial pressure thereof may be lowered so as to be easily evaporated, but it is more efficient as the purity of the raw material is higher from the viewpoint that the heat applied is used only for heating the raw material. The flow velocity and flow rate of the raw material gas are determined so as to match with the retention time in and heat supplying capacity of the thermal decomposition reactor to be described later, but it is selected in a range of from 0.1 m/sec to 100 m/sec, preferably from 0.5 m/sec to 50 m/sec, and more preferably from 1 m/sec to 30 m/sec since entrainment at the time of evaporation increases and a condensation product is likely to be formed on the wall surface, the pressure loss in the pipe increases, and the like when the flow velocity in the evaporator and the connecting pipe is too high.

2. Evaporator

In the method for producing N-vinylformamide using the production apparatus 1, first the raw material is evaporated by using the evaporator 10 and the raw material gas is thus generated. The evaporator 10 is not particularly limited, but a falling thin film evaporator or a rotary thin film evaporator is preferable from the viewpoint of shortening the retention time of the raw material. It is preferable that the evaporator 10 is provided with a mist collecting member and a collision plate for the purpose of preventing mist scattering.

An introduction pipe for raw material is attached to the upper side surface of the evaporator.

In addition, a pressure gauge is attached to the evaporator. The place to which the pressure gauge is attached may be any place, but for example, the pressure gauge may be attached to the upper portion of the evaporator. The pressure measured by this pressure gauge of the evaporator is taken as the pressure of evaporator. The pressure of the entire production apparatus 1 is substantially equal to the pressure of evaporator although there is slight loss at the bent portion of the pipe and the like.

Evaporation of the raw material is started as the evaporator is heated. It is preferable that the raw material is supplied to the evaporator and then heated to start the evaporation from the viewpoint of being able to prevent excessive heating of the evaporator.

The temperature when evaporating the raw material is usually 80° C. or more, preferably 100° C. or more, more preferably 110° C. or more, and it is usually 200° C. or less, preferably 180° C. or less, and more preferably 170° C. or less. More specifically, the temperature is preferably from 80° C. to 200° C. or less, more preferably from 100° C. to 180° C., and still more preferably from 110° C. to 170° C. By setting the temperature to be equal to or more than the lower limit, it is not required to excessively reduce the pressure of the evaporator and thermal decomposition reactor and it is thus not required to increase the size of the thermal decomposition reactor. It is preferable that the temperature is equal to or less than the upper limit from the viewpoint of being able to suppress the decomposition of the N-(α-alkoxyethyl)formamide in the evaporator.

In addition, it is preferable to conduct the evaporation under reduced pressure in order to evaporate the raw material at the temperature described above, and the pressure at this time is usually 3 mmHg or more, preferably 50 mmHg or more, and more preferably 70 mmHg or more and it is usually 500 mmHg or less, preferably 200 mmHg or less, and more preferably 150 mmHg or less. More specifically, the pressure is preferably from 3 to 500 mmHg, more preferably from 50 to 200 mmHg, and still more preferably from 70 to 150 mmHg. It is preferable that the pressure is equal to or more than the lower limit from the viewpoint that it is not required to excessively increase the vacuum pump power for reduction of pressure, the pressure loss is minor, it is also not required to increase the size of the thermal decomposition reactor in order to secure the retention time of the raw material gas in the thermal decomposition reactor, and the apparatus can be economically run. It is preferable that the pressure is equal to or less than the upper limit from the viewpoint that the boiling point does not excessively increase and decomposition of the raw material in the evaporator can be prevented.

It is desirable that the retention time of the raw material in the evaporator is as short as possible since the raw material is decomposed by heat when the retention time thereof is long. For this reason, a thin film evaporator is preferable. Examples of the thin film evaporator may include a falling thin film evaporator and vertical type and horizontal type thin film evaporators which forcibly form a thin film. The retention time of the raw material depends on the temperature as well, but it is preferable to evaporate the raw material by heating it for 1 hour or less, preferably 30 minutes or less, and more preferably several minutes or less.

3. First Connecting Pipe

The first connecting pipe 40 is not particularly limited as long as it can connect the evaporator 10 with the thermal decomposition reactor 20.

The first connecting pipe 40 is provided with heating means (not illustrated) for heating the pipe wall and thus adjusting the temperature of the pipe wall to a desired temperature. Examples of the heating means may include an electric heater, a jacket through which a heating medium can flow, and induction heating. Among these, a jacket or an electric heater is preferable from the viewpoint that it can evenly heat the pipe wall and is inexpensive.

Furthermore, the first connecting pipe 40 is provided with equipment for measuring the temperature of the pipe wall. In the case of using an electric heater as the heating means, a sheath pipe of a thermocouple or the like is welded to the pipe wall and a thermometer such as a thermocouple is attached thereto to measure the temperature of the pipe wall. In a case in which a fluid is allowed to flow through the jacket for heating, the temperature of the fluid at the outflow portion is measured in a state in which the steady state of fluid is sufficiently attained at the time of working and this is taken as the temperature of the pipe wall. The measurement location may be any location of the first connecting pipe 40.

It is preferable that at least a part of the first connecting pipe 40 is inclined upward and is connected to the lower portion of the evaporator 10. The evaporator 10 and the thermal decomposition reactor 20 can be disposed with a difference in height as at least a part of the first connecting pipe 40 positioned at the lower portion is inclined upward. In such a disposition state, the liquid raw material flowing down in the evaporator and the vaporized raw material come into concurrent contact with each other and it is thus possible to avoid entrainment that the liquid raw material splashes in the first connecting pipe. Furthermore, it is possible to decrease the bending angle of the pipe to be a cause of pressure loss and to easily introduce the raw material gas into the thermal decomposition reactor.

The temperature of the pipe wall of the first connecting pipe 40 is preferably less than 600° C. and more preferably less than 550° C. It is possible to suppress side reactions by setting the temperature to the above temperature.

4. Thermal Decomposition Reactor

The raw material gas generated in the evaporator 10 passes through the first connecting pipe 40 and is introduced into the thermal decomposition reactor 20.

In the invention, the thermal decomposition reaction is an endothermic reaction, thus the pipe wall is cooled unless sufficient heat is supplied thereto, and in that case, the condensed component is condensed and resin is likely to be formed. For this reason, it is required to supply heat as much as the quantities for the sensible heat and endothermic reaction so that the temperature of the inner wall of the thermal decomposition reactor 20 is sufficiently higher than the dew point.

As the thermal decomposition reactor 20, one having a tubular structure is generally used and it may be an empty tower or a packed tower. One having a multitubular structure is preferable in order to increase the heat transfer area, but the thermal decomposition reactor is not limited to this type. Examples of the heating medium may include a gas, a molten salt, heating using a heater, and induction heating.

The raw material gas introduced into the thermal decomposition reactor 20 is subjected to vapor phase thermal decomposition in the thermal decomposition reactor 20 to be converted into a thermally decomposed gas. In the thermal decomposition reactor 20, the raw material gas is subjected to intramolecular elimination by the vapor phase thermal decomposition reaction and N-vinylformamide is thus formed. The compound to be eliminated by intramolecular elimination is an alcohol corresponding to the alkoxy group, for example, in the case of using a N-(α-alkoxyethyl)formamide as the raw material and it is hydrogen cyanide in the case of using N-(α-cyanoethyl)formamide as the raw material. Formamide is formed as a byproduct in a case in which ethylenebisformamide is thermally decomposed. Hence, the thermally decomposed gas contains a gaseous elimination product (an alcohol, hydrogen cyanide, formamide, or the like) in addition to gaseous N-vinylformamide.

The temperature at the time of vapor phase thermal decomposition is usually 300° C. or more, preferably 350° C. or more, and more preferably 370° C. or more and it is usually 600° C. or less, preferably 570° C. or less, and more preferably 550° C. or less. More specifically, the temperature is preferably from 300° C. to 600° C., more preferably from 350° C. to 570° C., and still more preferably from 370° C. to 550° C. It is preferable that the temperature is equal to or more than the lower limit from the viewpoint of increasing the percent conversion and selectivity coefficient of the reaction. It is preferable that the temperature is equal to or more than the upper limit from the viewpoint of suppressing side reactions.

In addition, vapor phase thermal decomposition may be conducted under any of increased pressure, atmospheric pressure, or reduced pressure, but it is preferable to conduct the reaction under reduced pressure. In the case of conducting the reaction under reduced pressure, the pressure is usually 3 mmHg or more, preferably 50 mmHg or more, and more preferably 70 mmHg or more and it is usually 500 mmHg or less, preferably 200 mmHg or less, and more preferably 150 mmHg or less. More specifically, the pressure is preferably from 3 to 500 mmHg, more preferably from 50 to 200 mmHg, and still more preferably from 70 to 150 mmHg. It is preferable that the pressure is equal to or more than the lower limit from the viewpoint that the retention time of the gas in the thermal decomposition reactor is not too short. It is preferable that the pressure is equal to or less than the upper limit from the viewpoint that the evaporation temperature in the evaporator is not too high.

The linear velocity of the gas in the thermal decomposition reactor is from 0.1 m/sec to 100 m/sec, preferably from 0.5 m/sec to 50 m/sec, and more preferably from 1 m/sec to 30 m/sec.

The retention time of the thermally decomposed gas in the thermal decomposition reactor depends on the heat transfer coefficient of the thermal decomposition reactor as well, but it is generally 0.1 second or more and preferably 0.2 second or more and it is 10 seconds or less and preferably 5 seconds or less. More specifically, the retention time is preferably from 0.1 to 10 seconds and more preferably from 0.2 to 5 seconds. It is required to raise the temperature of the reaction gas to 300° C. or more required for decomposition and to maintain the temperature for the retention time required for the decomposition reaction.

It is preferable that the temperature of the pipe wall of the thermal decomposition reactor is set to be higher than the temperature of the reaction gas passing through the thermal decomposition reactor. Specifically, the temperature of the pipe wall of the thermal decomposition reactor is set to be higher than the temperature of the reaction gas passing through the thermal decomposition reactor preferably by 10° C. and more preferably by 50° C. By setting the temperature as described above, it is possible to prevent the process gas from being cooled and condensed.

The temperature of the heating medium of the thermal decomposition reactor is set to be higher than the temperature of the pipe wall of the first connecting pipe preferably by 10° C. or more and more preferably by 50° C. or more. By setting the temperature as described above, it is possible to maintain the temperature of the reaction pipe wall higher than the temperature of the process gas in the reaction pipe.

Incidentally, the temperature of the heating medium can be determined by measuring the medium temperature at the inlet and the outlet and calculating the logarithmic mean of the temperatures.

5. Second Connecting Pipe

The second connecting pipe 50 is not particularly limited as long as it can connect the thermal decomposition reactor 20 with the condenser 30.

The second connecting pipe 50 is provided with heating means (not illustrated) for heating the pipe wall and thus adjusting the temperature of the pipe wall to a desired temperature. Examples of the heating means may include an electric heater, a jacket through which a heating medium can flow, and induction heating. Among these, a jacket or an electric heater is preferable from the viewpoint that it can evenly heat the pipe wall and is inexpensive.

Furthermore, the second connecting pipe 50 is provided with equipment for measuring the temperature of the pipe wall. In the case of using an electric heater as the heating means, a sheath pipe of a thermocouple or the like is welded to the pipe wall and a thermometer such as a thermocouple is attached thereto to measure the temperature of the pipe wall. In a case in which a fluid is allowed to flow through the jacket for heating, the temperature of the fluid at the outflow portion is measured in a state in which the steady state of fluid is sufficiently attained at the time of working and this is taken as the temperature of the pipe wall. The measurement location may be any location of the second connecting pipe 50.

The temperature of the pipe wall of the second connecting pipe 50 is preferably less than 600° C. and more preferably less than 550° C. It is possible to suppress side reactions by setting the temperature to the above temperature.

6. Condenser

The process gas which has passed through the thermal decomposition reactor 20 passes through the second connecting pipe 50 and is introduced into the condenser 30.

The condenser 30 is not particularly limited, but examples thereof may include a condenser by indirect cooling using a cooling medium and a condenser by spray-type direct cooling spraying a cooled liquid.

A vacuum pump for reducing the pressure of the production apparatus 1 is attached to the outlet for the condensate in the condenser 30.

The process gas introduced into the condenser 30 is condensed and a mixture containing N-vinylformamide is thus obtained.

It is desirable that the temperature of the process gas is maintained at a temperature equal to or more than the temperature of the pipe wall of the second connecting pipe 50 satisfying Equation (1) to be described later in the second connecting pipe 50 and then the process gas is rapidly cooled in the condenser 30.

The temperature of the condensate in the condenser 30 is usually 50° C. or less, preferably 30° C. or less, and more preferably 20° C. or less, and the process gas is rapidly cooled to this temperature. Basically, the decomposition is more suppressed as the temperature of the condensate is lower, but the temperature of the condensate is usually −20° C. or more since the cost of cooling medium and the cost for cooling the cooling medium increase when the temperature set is too low.

7. Temperature of Pipe Wall of Connecting Pipe

In the invention, the temperature of the pipe wall of the first connecting pipe 40 preferably satisfies the following Equation (1) and more preferably satisfies the following Equation (2).

temperature of pipe wall (° C.)≥0.37×pressure of evaporator (mmHg)+205    Equation (1):

temperature of pipe wall (° C.)≥0.37×pressure of evaporator (mmHg)+210    Equation (2):

The effect of the invention is obtained by this, but it is preferable to start evaporation of the raw material in a state in which the first connecting pipe 40 satisfies Equation (1) above and it is more preferable to start evaporation of the raw material in a state in which the first connecting pipe 40 satisfies Equation (2) above.

In addition, it is preferable to start evaporation of the raw material in a state in which the first connecting pipe 40 satisfies Equation (1) above and it is more preferable to start evaporation of the raw material in a state in which the first connecting pipe 40 satisfies Equation (2) above. In other words, it is preferable that Equation (1) or Equation (2) above is satisfied from the start to the completion of evaporation of the raw material.

In the invention, a sheath pipe of a thermocouple or the like is welded to the pipe wall and a thermometer such as a thermocouple is attached thereto to measure the temperature of the pipe wall in the case of using an electric heater as the heating means. In a case in which a fluid is allowed to flow through the jacket for heating, the temperature of the fluid at the outflow portion is measured in a state in which the steady state of fluid is sufficiently attained at the time of working and this is taken as the temperature of the pipe wall.

The pressure of the thermal decomposition reactor is the same as that of the evaporator described above, and it is 3 mmHg or more and preferably 50 mmHg or more and it is 500 mmHg or less and preferably 200 mmHg or less. More specifically, the pressure is preferably from 3 to 500 mmHg and more preferably from 50 to 200 mmHg. It is preferable that the pressure is equal to or more than the lower limit from the viewpoint of being able to secure the retention time of gas in the thermal decomposition reactor without increasing the size of the thermal decomposition reactor. When the pressure is equal to or less than the upper limit, it is not required to excessively raise the evaporation temperature of raw material in the evaporator and thus decomposition of the raw material is suppressed and the temperature of the pipe wall of the pipe is also not required to be increased.

As described above, the raw material gas is thermally decomposed in the thermal decomposition reactor 20 and N-vinylformamide is formed by intramolecular elimination, but there is a case in which adhered substances called resin is generated particularly in the connecting pipes 40 and 50 at this time. In the prior art, it has been considered that the temperature of the pipe wall is raised in order to lower the viscosity of the condensed fluid and thus to enhance the fluidity and the temperature of the pipe wall may be equal to or higher than the boiling point of the raw material unless there is a cooling portion to cool the pipe wall by standing or the like. In fact, however, the effect of resin prevention is exhibited for the first time when the temperature of the pipe wall is raised to the temperature which is expressed by Equation (1) and is higher than the boiling point of the raw material before evaporation of the raw material is started.

The cause of this has been investigated, and as a result, it has been presumed that N-vinylformamide of the reaction product forms a product having a high boiling point particularly at a low temperature as a condensation reaction between one N-vinylformamide and another N-vinylformamide or between N-vinylformamide and the N-(α-substituted-ethyl)formamide of the raw material takes place and the dew point of the process gas increases. It is estimated that a product having a high boiling point adheres to the pipe wall and the formation of resin starts from this location when the temperature of the pipe wall is lower than the dew point of the process gas. In addition, once resin is formed, the resin growth starts from this location, and thus it is impossible to suppress the formation of resin even though the temperature is raised to be equal to or more than the dew point of the product which has a high boiling point and is a cause of resin after that. Hence, it is important to raise the temperature of the pipe wall before the reaction is started so that resin is not formed from the beginning. Generally it has been considered that burning of fluid on the pipe wall occurs when heat is applied since N-vinylformamide has a boiling point of 200° C. or more at ordinary pressure and is decomposed at 220° C. However, the boiling point of N-vinylformamide decreases and N-vinylformamide is gasified by conducting the thermal decomposition reaction under reduced pressure, and it is thus possible to heat the pipe wall to a temperature equal to or more than the dew point of the product which has a high boiling point and is a cause of without causing burning.

The raw material gas is heated even while the raw material gas passes through the first connecting pipe 40, thus the thermal decomposition reaction slightly proceeds in the first connecting pipe 40 as well to form N-vinylformamide, and this undergoes condensation to cause the reaction described above. In addition, it is considered that a temperature at which the equilibrium shifts from N-vinylformamide once formed to a condensation product is attained in the process of cooling N-vinylformamide formed and a condensation product is generated in the second connecting pipe 50 as well. This condensation product is again thermally decomposed into N-vinylformamide at approximately from 300° C. to 350° C. or more, and thus the formation of resin due to the formation of condensation product mainly occurs not in the main body of the thermal decomposition reactor but in the connecting pipes 40 and 50. In order to suppress this formation of resin, it is required to heat the pipe wall according to not the boiling points of the raw material and the product but Equation (1).

It is usually prone to be considered that burning of the liquid formed by condensation of the process gas is accelerated when the pipe wall is heated. However, the inventors of the invention have not been caught by such common sense but have come to grasp the fact that dew condensation of a product which has a high boiling point and is contained in the process gas is the beginning of formation of condensation product and it is effective to suppress the dew condensation in order to prevent burning. Moreover, as a result of extensive investigations, it has been found out that it is effective to heat the pipe wall since dew condensation of a fluid product having a high boiling point leads to the formation of coagulated solid in the present reaction apparatus. Furthermore, it has been discovered that the temperature of the pipe wall required to suppress the formation of resin is present in the temperature which is expressed by Equation (1) and is higher than the boiling point of the raw material or the product since a product which has a high boiling point and is formed during heating or cooling causes the formation of resin.

It has been demonstrated that the dew point of a product having a high boiling point varies depending on the abundance, abundance molar ratio, boiling point, and the like thereof but there is a relation between the dew point of a product having a high boiling point and the pressure of dew point of product having high boiling point (° C.)=0.37× pressure of evaporator (mmHg)+200. For this reason, it is possible to prevent dew condensation of a product component having a high boiling point by setting the temperature of the pipe wall to be higher than the temperature to be calculated by the above equation by 5° C. or 10° C.

With regard to the temperature of the pipe wall of the second connecting pipe 50, the temperature of the process gas heated in the thermal decomposition reactor is sufficiently high and thus the process gas may reach the condenser without being cooled to a temperature equal to or less than the dew point.

Specifically, it is preferable that the temperature of the pipe wall of the second connecting pipe 50 satisfies Equation (1) above and more preferably satisfies Equation (2) above.

In addition, in order to obtain a higher effect of the invention, it is preferable to start evaporation of the raw material in a state in which the second connecting pipe 50 satisfies Equation (1) above and it is more preferable to start evaporation of the raw material in a state in which the second connecting pipe 50 satisfies Equation (2) above. Furthermore, it is preferable to start evaporation of the raw material in a state in which the first connecting pipe 40 and the second connecting pipe 50 satisfy Equation (1) above and it is more preferable to start evaporation of the raw material in a state in which the first connecting pipe 40 and the second connecting pipe 50 satisfy Equation (2) above.

In addition, it is preferable to start evaporation of the raw material in a state in which the second connecting pipe 50 satisfies Equation (1) above and it is more preferable to start evaporation of the raw material in a state in which the second connecting pipe 50 satisfies Equation (2) above. Furthermore, it is preferable to start evaporation of the raw material in a state in which the first connecting pipe 40 and the second connecting pipe 50 satisfy Equation (1) above and it is more preferable to start evaporation of the raw material in a state in which the first connecting pipe 40 and the second connecting pipe 50 satisfy Equation (2) above. In other words, it is preferable that Equation (1) or Equation (2) above is satisfied from the start to the completion of evaporation of the raw material.

In the method for producing N-vinylformamide of the invention described above, it is possible to suppress the process gas from being liquefied and adhering to the inner wall and to suppress the formation of a condensation product of N-vinylformamide by a side reaction as the temperature of the pipe wall of the first connecting pipe satisfies Equation (1) or Equation (2) above.

Consequently, according to the method for producing N-vinylformamide of the invention, it is possible to suppress the formation of a condensation product and to stably produce N-vinylformamide.

EXAMPLES

Hereinafter, the invention will be specifically described with reference to Examples, but the invention is not limited thereto.

Example 1

By using the production apparatus 1 illustrated in FIG. 1, N-vinylformamide was produce by thermally decomposing N-(α-methoxyethyl)formamide in the following manner.

The evaporator 10 and the thermal decomposition reactor 20 were connected with each other via the first connecting pipe 40 and the thermal decomposition reactor 20 and the condenser 30 were connected with each other via the second connecting pipe 50 equipped with an electric heater (not illustrated).

A ribbon-like heater was wound around the outer wall of the first connecting pipe 40, the outside thereof was maintained warm with a heat insulating material, and the apparatus was worked. A sheath pipe for inserting a thermocouple was welded to the middle portion (portion B) of the connecting pipe, a thermocouple was inserted thereinto, the temperature of the pipe wall was measured, the heater was adjusted based on this temperature so that the temperature of the pipe wall was 350° C., and the apparatus was worked.

Meanwhile, an electrically heated wire was wound around the second connecting pipe, the outer wall of the second connecting pipe was insulated with a heat insulating material, and the second connecting pipe 50 was heated. Furthermore, a thermocouple was inserted into a sheath pipe welded to the middle portion (portion E) of the second connecting pipe 50, the temperature was measured, the heater was adjusted based on this temperature so that the temperature of the pipe wall was 350° C., and the apparatus was worked.

While reducing the pressure of the entire production apparatus 1 to 138 mmHg from the outlet of the thermal decomposition reactor 20 (the part connected with the second connecting pipe 50), N-(α-methoxyethyl)formamide supplied to the evaporator 10 was evaporated to form a raw material gas, and the raw material gas was supplied to the thermal decomposition reactor 20 through the first connecting pipe 40.

The evaporator was humidified using pressurized steam at 13 KG. The evaporation temperature of N-(α-methoxyethyl)formamide evaporated was 160° C.

The pipe wall of the thermal decomposition reactor was heated using nitrogen gas heated at 500° C.

The raw material gas supplied to the thermal decomposition reactor 20 was thermally decomposed by the vapor phase thermal decomposition reaction and the thermally decomposed gas thus obtained was supplied to the condenser 30 through the second connecting pipe 50. The temperature of the condensate was 20° C.

Working of condensing the thermally decomposed gas supplied to the condenser 30 and obtaining a mixture (condensed thermal decomposition products) containing N-vinylformamide was conducted for 100 hours. Thereafter, the working was stopped and the appearance of the inner wall of the first connecting pipe 40 and the inner wall of the second connecting pipe 50 was observed, and the results are presented in Table 1.

Example 2

The same operation as in Example 1 except that the pressure of evaporator was set to 130 mmHg and the temperature of the pipe wall of the first connecting pipe was set to 300° C. was conducted, the appearance of the inner walls of the first connecting pipe and the second connecting pipe was observed, and the results are presented in Table 1.

Example 3

The same operation as in Example 1 except that the pressure of evaporator was set to 130 mmHg and the temperature of the pipe wall of the first connecting pipe was set to 270° C. was conducted, the appearance of the inner walls of the first connecting pipe and the second connecting pipe was observed, and the results are presented in Table 1.

Comparative Example 1

The same operation as in Example 1 except that the pressure of evaporator was set to 80 mmHg and the temperature of the pipe wall of the first connecting pipe was set to 230° C. was conducted, the appearance of the inner walls of the first connecting pipe and the second connecting pipe was observed, and the results are presented in Table 1.

Comparative Example 2

The same operation as in Example 1 except that the pressure of evaporator was set to 130 mmHg and the temperature of the pipe wall of the first connecting pipe was set to 250° C. was conducted, the appearance of the inner walls of the first connecting pipe and the second connecting pipe was observed, and the results are presented in Table 1.

Comparative Example 3

The same operation as in Example 1 except that the pressure of evaporator was set to 138 mmHg and the temperature of the pipe wall of the first connecting pipe was set to 210° C. was conducted, the appearance of the inner walls of the first connecting pipe and the second connecting pipe was observed, and the results are presented in Table 1.

Comparative Example 4

The same operation as in Example 1 except that the pressure of evaporator was set to 138 mmHg and the temperature of the pipe wall of the first connecting pipe was set to 190° C. was conducted, the appearance of the inner walls of the first connecting pipe and the second connecting pipe was observed, and the results are presented in Table 1.

Comparative Example 5

The same operation as in Example 1 except that the pressure of evaporator was set to 138 mmHg and the temperature of the pipe wall of the first connecting pipe was set to 120° C. was conducted, the appearance of the inner walls of the first connecting pipe and the second connecting pipe was observed, and the results are presented in Table 1.

Comparative Example 6

The same operation as in Example 1 except that the pressure of evaporator was set to 130 mmHg and the temperature of the pipe wall of the first connecting pipe was set to 200° C. was conducted, the appearance of the inner walls of the first connecting pipe and the second connecting pipe was observed, and the results are presented in Table 1.

Example 4

The same operation as in Example 1 except that the pressure of evaporator was set to 80 mmHg, the connecting pipe 40 was changed to a double pipe in the apparatuses used in Example 1, and hot nitrogen at 500° C. was allowed to flow through the jacket was conducted, the appearance of the inner walls of the first connecting pipe and the second connecting pipe was observed, and the results are presented in Table 1. At this time, the temperature at the outlet for gas of the jacket was set to the wall temperature of the connecting pipe 40, and the temperature was 240° C.

Comparative Example 7

The same operation as in Example 1 except that the pressure of evaporator was set to 80 mmHg, the same apparatus as in Example 4 was used, and hot nitrogen at 400° C. was allowed to flow through the jacket was conducted, the appearance of the inner walls of the first connecting pipe and the second connecting pipe was observed, and the results are presented in Table 1. At this time, the temperature at the outlet for gas of the jacket was 190° C.

TABLE 1

|  | Pressure of evaporator mmHg | Temperature of pipe wall calculated from pressure of evaporator and Equation (1) ° C. | Temperature of pipe wall calculated from pressure of evaporator and Equation (2) ° C. | Wall temperature of first connecting pipe ° C. | Wall temperature of second connecting pipe ° C. | Presence or absence of resin First connecting pipe | Presence or absence of resin Second connecting pipe | Operation time |
|---|---|---|---|---|---|---|---|---|
| Example 1 | 138 | 256 | 261 | 350 | 350 | Absent | Absent | 100 hours |
| Example 2 | 130 | 253 | 258 | 300 | 350 | Absent | Absent | 100 hours |
| Example 3 | 130 | 253 | 258 | 270 | 350 | Absent | Absent | 100 hours |
| Example 4 | 80 | 235 | 240 | 240 | 350 | Absent | Absent | Half year |
| Comparative Example 1 | 80 | 235 | 240 | 230 | 350 | Slightly present | Absent | 24 days |
| Comparative Example 2 | 130 | 253 | 258 | 250 | 350 | Slightly present | Absent | 100 hours |
| Comparative Example 3 | 138 | 256 | 261 | 210 | 350 | Present | Absent | 17 days |
| Comparative Example 4 | 138 | 256 | 261 | 190 | 350 | Present | Absent | 17 days |
| Comparative Example 5 | 138 | 256 | 261 | 120 | 350 | Present | Absent | 17 days |
| Comparative Example 6 | 130 | 253 | 258 | 200 | 350 | Present | Absent | 100 hours |
| Comparative Example 7 | 80 | 235 | 240 | 190 | 350 | Present | Absent | Half year |

In the respective Examples, the temperature of the first connecting pipe is set to be higher than the temperature of the pipe wall to be calculated by Equation (1), thus there is no adhered substances, the quality of the product obtained does not decrease, and stable working is possible in each working time. In Comparative Examples, the temperature of the first connecting pipe was set to be lower than the temperature of the pipe wall to be calculated by Equation (1) and thus adhered substances are observed on the connecting pipe.

INDUSTRIAL APPLICABILITY

According to the method for producing N-vinylformamide of the invention, it is possible to suppress the formation of a condensation product and to stably produce N-vinylformamide. Stopping for cleaning the resin-storing container and the first connecting pipe and restarting operation are unnecessary, thus there is no possibility of a decrease in the production amount and a fluctuation in the quality which result from the stopping and restarting operation and the cost of plant repair such as cleaning can also be cut down. In addition, it is also possible to suppress a decrease in the quality and a fluctuation in the stability of N-vinylformamide which result from the decomposition products to be volatilized from the condensation product adhered and the condensation product flowed down in the container. Furthermore, it is possible to prevent loss of raw material due to the formation of a condensation product, and the yield of N-vinylformamide is thus improved.

EXPLANATIONS OF LETTERS OR NUMERALS

1 APPARATUS FOR PRODUCING N-VINYLFORMAMIDE
    10 EVAPORATOR
    20 THERMAL DECOMPOSITION REACTOR
    30 CONDENSER
    40 FIRST CONNECTING PIPE
    50 SECOND CONNECTING PIPE

The invention claimed is:

1. A method for producing N-vinylformamide by a vapor phase thermal decomposition reaction using an evaporator for evaporating a raw material, a thermal decomposition reactor for thermally decomposing a raw material gas generated by the evaporator, and a condenser for condensing a thermally decomposed gas obtained by the thermal decomposition reactor, wherein
    evaporation of the raw material in the evaporator is started in a state in which a temperature of a pipe wall of a first connecting pipe for connecting the evaporator with the thermal decomposition reactor satisfies the following Equation (1):

$$\text{temperature of pipe wall (° C.)} \geq 0.37 \times \text{pressure of evaporator (mmHg)} + 205 \quad \text{Equation (1):}$$

2. The method for producing N-vinylformamide according to claim 1, wherein evaporation of the raw material in the evaporator is started in a state in which a temperature of a pipe wall of a second connecting pipe for connecting the thermal decomposition reactor with the condenser satisfies Equation (1) above.

3. The method for producing N-vinylformamide according to claim wherein the raw material is a N-($\alpha$-substituted-ethyl)formamide.

4. The method for producing N-vinylformamide according to claim 3, wherein the N-($\alpha$-substituted-ethyl)formamide is a N-($\alpha$-alkoxyethyl)formamide.

5. The method for producing N-vinylformamide according to claim 2, wherein evaporation of the raw material in the evaporator is started in a state in which temperatures of pipe walls of the first connecting pipe and the second connecting pipe satisfy the following Equation (2):

$$\text{temperature of pipe wall (° C.)} \geq 0.37 \times \text{pressure of evaporator (mmHg)} + 210. \quad \text{Equation (2):}$$

6. The method for producing N-vinylformamide according to claim 1, wherein a temperature of a pipe wall of the thermal decomposition reactor is higher than a temperature of a reaction gas passing through the thermal decomposition reactor.

7. The method for producing N-vinylformamide according to claim 1, wherein a temperature of a heating medium of the thermal decomposition reactor is higher than the temperature of the pipe wall of the first connecting pipe by 10° C. or more.

8. The method for producing N-vinylformamide according to claim 2, wherein temperatures of pipe walls of the first connecting pipe and the second connecting pipe are less than 600° C.

9. The method for producing N-vinylformamide according to claim 4, wherein a flow velocity of N-($\alpha$-alkoxyethyl)formamide gas is in a range of from 0.1 m/sec to 100 m/sec.

10. The method for producing N-vinylformamide according to claim 1, wherein a part of the first connecting pipe is inclined upward and is connected to a lower portion of the evaporator.

* * * * *